Figure 1:
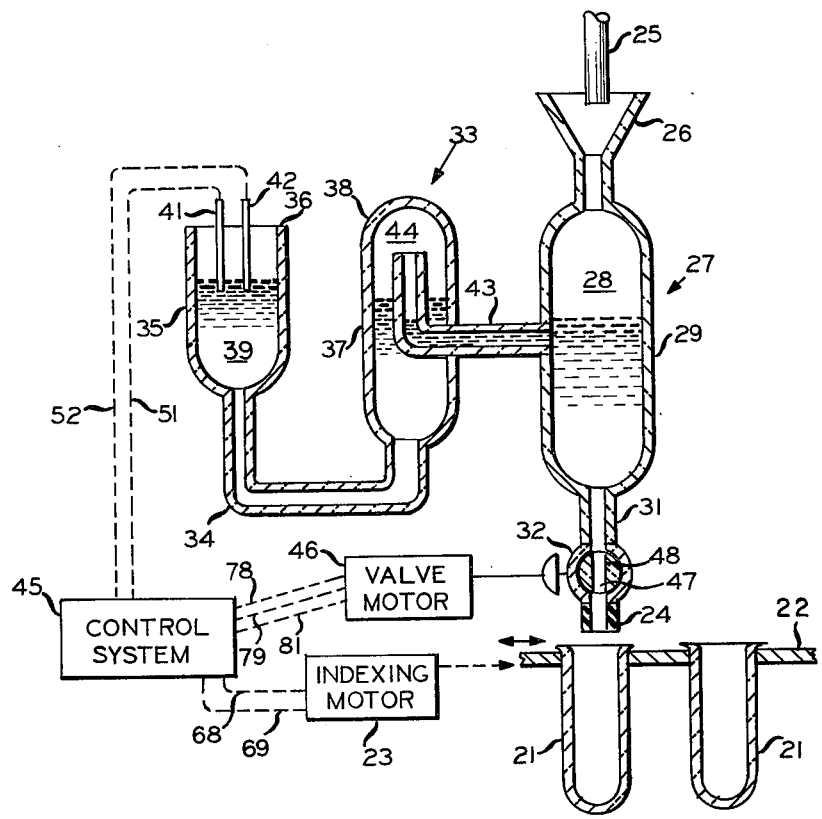

United States Patent [19]

Vinatieri

[11] 4,019,545
[45] Apr. 26, 1977

[54] SAMPLE FRACTION COLLECTOR
[75] Inventor: James E. Vinatieri, Bartlesville, Okla.
[73] Assignee: Phillips Petroleum Company, Bartlesville, Okla.
[22] Filed: Dec. 29, 1975
[21] Appl. No.: 645,180
[52] U.S. Cl. .............................. 141/130; 23/259 R; 73/223; 141/153; 222/70; 222/425
[51] Int. Cl.² ..................... B65B 3/36; B65B 43/60
[58] Field of Search ................... 23/259 R; 73/223; 127/101.25; 141/1, 129–131, 153, 196, 198, 324; 222/70, 425

[56] References Cited
UNITED STATES PATENTS

| 3,088,315 | 5/1963 | Withers | 73/223 X |
| 3,672,479 | 6/1972 | Schwertfeger | 222/70 X |

Primary Examiner—Richard E. Aegerter
Assistant Examiner—Frederick R. Schmidt

[57] ABSTRACT

A sample fraction collector for sequentially collecting a plurality of samples of uniform volume despite variations in sample flow rate and/or viscosity comprises means defining a sample chamber, an outlet conduit means having a rotatable valve means therein, rack means for sequentially positioning a plurality of individual receptacles beneath a dispensing outlet of said outlet conduit means, a generally U-shaped tube for holding an electrolytic solution with first and second electrode means positioned in one leg and a pressure tube communicating between the other leg and the sample chamber. A control system is actuated by the electrolytic solution contacting both electrode means to energize the rack means to the next position and then to rotate the valve means to the open position for a period of time to drain the sample chamber.

5 Claims, 3 Drawing Figures

SAMPLE FRACTION COLLECTOR

This invention relates to liquid fraction sample collectors and more particularly to fraction collectors for sequentially dispensing a plurality of samples of controlled volume.

U.S. Pat. No. 3,181,574 discloses a fraction collector for sequentially dispensing a plurality of liquid samples of uniform volume. This collector provides operating difficulties with highly viscous fluids since the inlet and outlet apertures are relatively small and cannot be fully opened due to the presence of the plunger valve element in the openings as well as the contact of the sample liquid with the plunger valve element. Furthermore, when sampling an oily liquid with a wide range of surface tensions, e.g. an oil-water-surfactant mixture, the low surface tension fluids are apt to leak through the seal between the plunger and aperture. Rubber gaskets cannot be used here since they would swell with oil. This collector senses the liquid level in the sample chamber and will be sensitive to the curvature of the meniscus, which is a function of surface tension.

One of the commercially available automatic fraction collectors employs means for positioning an electrolytic solution in response to the hydrostatic pressure of the sample liquid being collected, with the level sensing electrodes being associated with the electrolytic solution. This permits the use of the electrical level sensing electrodes with nonelectrolytic sample liquids. However, this fraction collector utilizes a siphon to dump the liquid sample which has accumulated in the sample collection chamber. The siphon action presents operating difficulties for sample liquids having low surface tension, such as surfactant solutions.

It is an object of the present invention to provide a liquid fraction sample collector for sequentially dispensing a plurality of liquid samples of uniform volume despite variation in the flow rate, viscosity and/or surface tension of the sample liquid. It is an object of the invention to provide such a collector having a sample collection chamber with a valved outlet means wherein the valve element is rotatable rather than a plunger valve element. Another object of the invention is to provide such a collector suitable for use with oil-water-surfactant mixtures. A further object of the invention is to provide a valved sample fraction dispensing head with means for electrically determining the level of nonelectrolytic liquids. Yet another object of the invention is to provide such a fraction collector which does not require a moving valve element in the sample collection chamber. A further object of the invention is to provide a low cost, reliable, and compact control system for a fraction collector. Other objects, aspects and advantages of the invention will be apparent from a study of the specification, the drawings and the appended claims to the invention.

Figure 2:
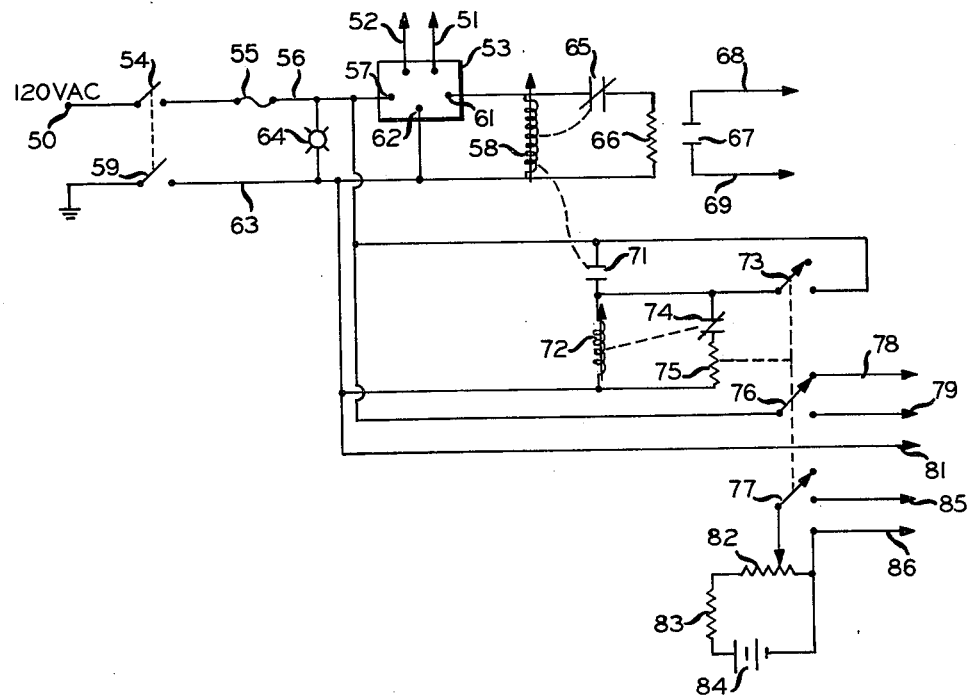
Figure 3:
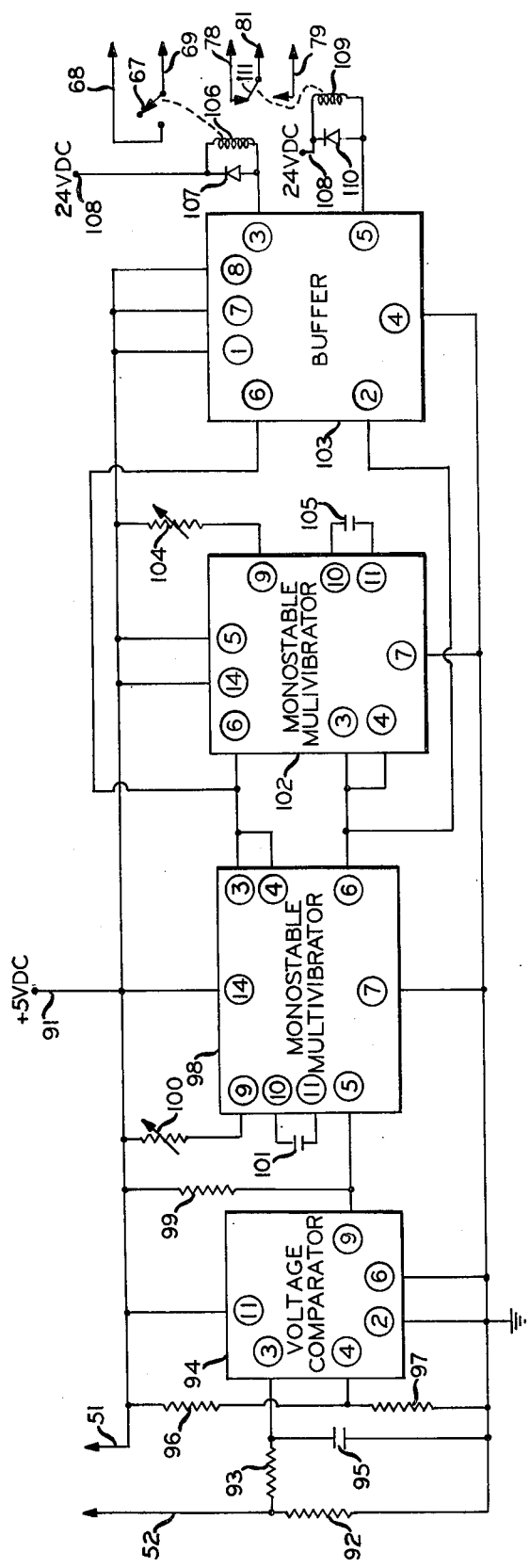

In the drawings,

FIG. 1 is a diagrammatic illustration, partly in vertical cross-section of a fraction collector for viscous fluids in accordance with the present invention; and FIGS. 2 and 3 are alternate embodiments of a control system for the fraction collector of FIG. 1.

Referring now to FIG. 1 in detail, a plurality of test tubes 21 are supported on a predetermined array in a rack 22. An indexing motor 23 is operatively connected to rack 22 to intermittently move rack 22 in a step-wise fashion such that test tubes 21 are individually positioned beneath the sample fluid discharge spout 24 in a predetermined sequence. The liquid material being sampled is passed continuously from a source thereof through supply conduit 25 into the funnel-shaped inlet 26 of a measured volume dispensing head 27. The measuring chamber 28 of head 27 is defined by wall means 29 of suitable configuration and an outlet conduit 31. In a presently preferred embodiment, at least a portion of wall means 29 is transparent to permit visual observation of the sample liquid in the chamber 28. The interior of inlet 26 is in fluid communication with an upper portion of chamber 28, while the interior of outlet conduit 31 is in fluid communication with the bottom of chamber 28. A rotatable ball valve 32 is connected between the lower end of conduit 31 and the upper end of discharge spout 24. When valve 32 is in the closed position, liquid from conduit 25 passing through inlet 26 into chamber 28 accumulates in chamber 28 until the desired volume of sample liquid in chamber 28 is achieved at which time rack 22 is actuated to move the next test tube 21 into position under the outlet of conduit 24. The valve 32 is moved to the open position to permit the accumulated volume of sample liquid to drain into the respective test tube 21 positioned beneath the outlet end of conduit 24. After the expiration of a predetermined drain interval, valve 32 is moved to the closed position.

The attainment of the desired volume of sample liquid in chamber 28 is ascertained by detector 33. Detector 33 comprises a generally U-shaped tube 34 having a substantially vertical first leg 35 with an open end 36 and a substantially vertical second leg 37 with a closed end 38 with liquid communication between said legs, an electrolytic solution 39 in tube 34 to partially fill each of legs 35 and 37, a pair of electrodes 41 and 42, and a generally L-shaped tube 43. Tube 43 provides fluid communication between the upper portion of leg 37 and chamber 28. Tube 43 connects with chamber 28 at a level substantially below the level reached by the desired volume of sample liquid in chamber 28 so that sample liquid enters tube 43. The other end of tube 43 extends into leg 37 and then upwardly towards the closed end 38 to a point above the maximum level of electrolytic solution 39 in leg 37 and also above the maximum level of sample liquid in chamber 28. When chamber 28 is empty, the level of electrolytic solution in leg 35 is below the lower end of at least one of electrodes 41 and 42. As the level of sample liquid in chamber 28 rises, sample liquid enters the lower portion of tube 43, causing an increase in the pressure in the air space 44 in the upper portion of leg 37, thereby causing a movement of part of the electrolytic solution from leg 37 toward leg 35. When the desired level of sample liquid is achieved in chamber 28, the electrolytic solution 39 in leg 35 contacts the lower ends of both of electrodes 41 and 42, thereby closing an electrical circuit in control system 45. Upon the attainment of the desired volume of sample liquid in chamber 28, as indicated by electrolytic solution contacting both of electrodes 41 and 42, control system 45 actuates indexing motor 23 to index rack 22 to the next position. Then control system actuates valve motor 46 to rotate ball valve 32 so that the passageway 47 in ball 48 of valve 32 provides liquid communication between conduits 31 and 24. At the end of the predetermined drain interval, control system 45 actuates valve motor 46 to rotate ball valve 32 so that passageway 47 no longer provides liquid communication between conduits 31 and 24.

Referring now to FIG. 2, an electromechanical embodiment of control system 45 is illustrated. Electrodes 41 and 42 are connected by wires 51 and 52 to the low voltage switch terminals of a safety switch 53. Safety switch 53 can be any suitable device, for example a normally open Safe-pak Switching Unit, 120 V/5 AMP, manufactured by Delaval Gems Sensors Division, Farmington, Conn. A switch 54, a fuse 55, and power wire 56 are connected in series between a suitable source 50 of A.C. voltage, e.g., 120 VAC, and the power input terminal 57 of safety switch 53. A time delay relay coil 58 and a switch 59 are connected in series between power output terminal 61 of safety switch 53 and ground. Ground terminal 62 of safety switch 53 is also connected through ground wire 63 and switch 59 to ground. A pilot light 64 can be connected between power wire 56 and ground wire 63. A normally closed switch 65 and a relay coil 66 are connected in series between terminal 61 and ground wire 63. A normally open switch 67, actuatable by relay coil 66, is connected between leads 68 and 69 to indexing motor 23. A normally open switch 71, actuatable by relay coil 58, and a time delay relay coil 72 are connected in series between power wire 56 and ground wire 63. A two position switch 73 is connected in parallel with switch 71. A normally closed switch 74, actuatable by relay coil 72, and a relay coil 75 are connected in series across the terminals of relay coil 72. Relay coil 75 actuates switch 73, two position switch 76 and two position switch 77. The contactor of switch 76 is connected to power wire 56. Lead wires 78 and 79 connect the two contact terminals of switch 76 to two control terminals of valve motor 46. A ground lead 81 connects ground wire 63 to valve motor 46. The contactor of switch 77 is connected to the contactor of potentiometer 82. Resistor 83 and potentiometer 82 are connected in series across the terminals of D.C. voltage source 84. Leads 85 and 86 connect one contact terminal of switch 77 and one end of potentiometer 82 to suitable recording means (not shown).

When switches 54 and 59 are closed and the electrolytic solution 37 contacts both of electrodes 41 and 42, electrical current passes through time delay relay coil 58, thereby opening switch 65 and closing switch 71, after the expiration of a first predetermined time period, the duration of which is determined by the setting of time delay relay coil 58. During this first predetermined time period, switch 65 remains closed, thereby passing electrical current through relay coil to close switch 67 to energize indexing motor 23. The length of this first predetermined time period is the length of time required for rack 22 to be indexed to the next position. At the end of this first predetermined time period, switch 65 opens, thereby opening switch 67 and deenergizing indexing motor 23. The closing of switch 71 at the end of the first predetermined time period permits the flow of electrical current through relay coil 72 and through normally closed switch 74 and relay coil 75. The flow of electrical current through relay coil 75 causes the closing of latching switch 73, the moving of the contactor of switch 76 from the "close" lead 78 to the "open" lead 79, and the closing of switch 77 to apply a voltage signal to the recording means. The closing of latching switch 73 provides a path for electrical current flow through relay coil 72 after switch 71 opens as a result of the draining of the sample liquid from chamber 28 causing the level of electrolytic solution to drop below at least one of electrodes 41 and 42, thereby interrupting the power to terminal 61. The deenergizing of relay coil 58 and the associated closing of switch 65 does not affect the indexing motor 23 in view of the lack of power at terminal 61. The movement of the contactor of switch 76 to the open lead 79 causes valve motor 46 to move ball valve 32 to the open position, thereby permitting the drainage of the sample liquid from chamber 28 into the respective test tube 21. After the expiration of a second predetermined time period beginning with the energization of time delay relay coil 72, normally closed switch 74 is moved to an open position by relay coil 72, thereby deenergizing relay coil 75 and causing switches 73, 76 and 77 to return to their original positions. The return of the contactor of switch 76 to the close lead 78 causes valve motor 46 to be actuated to move ball valve 32 to the closed position. The length of the second predetermined time period is determined by the setting of time delay relay coil 72 and corresponds to the drain interval for draining sample liquid from chamber 28. Time delay relay coils 58 and 72 can be any suitable devices, for example relay coil 58 can be a Potter and Brumfield CDB38-70003 (0.1 to 10 seconds range) and relay coil 72 can be a Potter and Brumfield CDB38-70004 (0.6 to 60 seconds range).

Referring now to FIG. 3, electrode lead 51 is connected to a terminal 91 of a source of 5 VDC while electrode lead 52 is connected through resistor 92 to ground and through resistor 93 to terminal 3 of voltage comparator 94 (a model LM311 voltage comparator manufactured by National Semiconductor Corp., Santa Clara, California). Terminal 3 of comparator 94 is also connected through capacitor 95 to ground. Terminal 4 of comparator 94 is connected through resistor 96 to terminal 91 and through resistor 97 to ground. Terminal 11 of comparator 94 is connected to terminal 91 while terminals 2 and 6 of comparator 94 are connected to ground. The output terminal 9 of comparator 94 is connected to input terminal 5 of monostable multivibrator 98 (a model SN74121 monostable multivibrator manufactured by Texas Instruments Inc., Dallas, Texas) and through resistor 99 to terminal 91. Terminal 9 of multivibrator 98 is connected through variable resistor 100 to terminal 91, while terminal 14 of multivibrator 98 is connected directly to terminal 91. A capacitor 101 is connected between terminals 10 and 11 of multivibrator 98. Terminal 7 of multivibrator 98 is connected to ground. Terminals 3 and 4 of multivibrator 98 are connected to terminal 6 of monostable multivibrator 102 (a model SN74121 monostable multivibrator manufactured by Texas Instruments Inc., Dallas, Texas) and to terminal 6 of buffer 103 (a model LM75452 dual peripheral driver manufactured by National Semiconductor Corp.). Terminal 6 of multivibrator 98 is connected to terminals 3 and 4 of multivibrator 102 and to terminal 2 of buffer 103. Terminals 5 and 14 of multivibrator 102 and terminals 1, 7 and 8 of buffer 103 are connected to terminal 91, while terminal 7 of multivibrator 102 and terminal 4 of buffer 103 are connected to ground. A variable resistance 104 is connected between terminal 9 of multivibrator 102 and terminal 91, while a capacitor 105 is connected between terminals 10 and 11 of multivibrator 102. Relay coil 106 and diode 107 are connected in parallel between terminal 3 of buffer 103 and terminal 108 of a source of 24 VDC. Energization of relay coil 106 causes switch 67 to close, thereby energizing indexing motor 23. A relay coil 109 and a diode 110 are connected in parallel between terminal 5 of buffer 103 and terminal 108. The energization of relay coil 109 moves the contactor of switch 111 from close lead 78 to open lead 79 to valve motor 46.

When the electrodes 41 and 42 are immersed in brine, the voltage at pin 3 of voltage comparator 94 rises to approximately 4.8 volts. This trips the voltage comparator 94 and the output at pin 9 goes high, activating monostable multivibrator 98. The output of multivibrator 98 is fed to buffer 103, which drives relay coil 106. The timing period of monostable multivibrator 98 is adjustable from 1 to 15 seconds by variable resistor 100 and is set to operate the indexing motor 23 just long enough to advance the rack 22 one position.

When multivibrator 98 times out and turns off, monostable multivibrator 102 is activated and operates relay coil 109 through buffer 103. This relay coil 109 opens the motorized ball valve 32 which can be held open from 3 to 60 seconds by adjusting variable resistance 104. The valve 32 can be held open long enough to allow even the most viscous polymer solutions to drain.

Multivibrator 98 and 102 are interlocked so they cannot both be on at the same time. This prevents false triggering of the system.

Reasonable variations and modifications are possible within the scope of the foregoing disclosure, the drawing and the appended claims to the invention. For example sample line 25 can be connected directly to dispensing head 27 by providing a suitable vent in the upper position of chamber 28. The rack 22 can have the sample receptacles positioned in a circular, spiral or rectalinear array.

I claim:

1. Apparatus for sequentially dispensing a plurality of uniform volume samples of a liquid material, comprising means defining a sample chamber having a sample inlet and a sample outlet; means for continuously introducing liquid to be sampled through said sample inlet into said sample chamber; valve means having a valve inlet, a valve outlet, and a rotatable valve element having a passageway therethrough to provide liquid communication between said valve inlet and said valve outlet when said valve element is in the open position and to block liquid communication between said valve inlet and said valve outlet when said valve element is in the closed position; means for rotating said valve element from each of said open and closed positions to the other of said open and closed positions; means connecting said valve inlet to said sample outlet; outlet conduit means connected to said valve outlet and having a dispensing end; rack means for sequentially positioning individual sample receptacles beneath said dispensing end of said outlet conduit means; a generally U-shaped tube having first and second substantially vertical legs with liquid communication therebetween, one of said legs having a closed end and the other of said legs having an open end; said U-shaped tube legs and ends being adapted to contain an electrolytic solution therein; a generally L-shaped tube extending from said means defining a sample chamber, at a level in said sample chamber substantially below the level reached in said sample chamber by the desired volume of sample liquid, into said one of said legs having a closed end and then upwardly toward said closed end to a point above the maximum level of electrolyte solution in said one of said legs having a closed end, to provide fluid communication between said sample chamber and the interior of the upper portion of said one leg; first and second electrode means positioned in said open end of the said other leg to contact the electrolytic solution when the desired volume of sample liquid has accumulated in said sample chamber; whereby sample liquid entering the generally L-shaped tube causes an increase in the fluid pressure in the closed end of said one leg, thereby causing movement of part of the electrolytic solution from said one leg toward said other leg, thereby causing said electrolytic solution to contact both of said first and second electrode means; and control means responsive to each occurrence of the electrolytic solution contacting both of said first and second electrode means to actuate said rack means to move a sample receptacle beneath said dispensing end of said outlet conduit means and then to actuate the valve element rotating means to rotate said valve element to the open position for a predetermined drain interval to drain the sample liquid accumulated in said sample chamber into the sample receptacle positioned beneath said dispensing end of said outlet conduit means.

2. Apparatus in accordance with claim 1 wherein said valve element is a ball having a passageway therethrough.

3. Apparatus in accordance with claim 2 wherein at least a portion of said means defining a sample chamber is transparent to permit visual observation of the sample liquid in said sample chamber.

4. Apparatus in accordance with claim 1 wherein said control means comprises first and second time delay relay means, means for applying electrical power to said first time delay relay means and to actuate said rack means upon the electrolytic solution contacting both of said electrode means, means responsive to said first time delay relay means to deenergize said rack means and to actuate said second time delay relay means and move said valve element to the open position after a first predetermined time period, and means responsive to said second time delay relay means to move said valve element to the closed position at the end of a second predetermined time period after the expiration of said first predetermined time period.

5. Apparatus in accordance with claim 1 wherein said control means comprises voltage comparator means, first and second monostable multivibrators, buffer means, and first and second relay means, said first monostable multivibrator being connected between said voltage comparator means and said buffer means to energize said first relay means to actuate said rack means, said second monostable multivibrator being connected between said voltage comparator and said buffer means to energize said second relay means to effect the rotation of said valve element.

* * * * *